United States Patent [19]

Barda

[11] Patent Number: 4,468,479
[45] Date of Patent: Aug. 28, 1984

[54] ESTER AND HALOGEN CONTAINING POLYOLS

[75] Inventor: Henry J. Barda, North Brunswick, N.J.

[73] Assignee: Ethyl Corporation, Richmond, Va.

[21] Appl. No.: 385,783

[22] Filed: Jun. 7, 1982

[51] Int. Cl.³ .................... C08G 18/14; C08G 18/46; C08G 63/68
[52] U.S. Cl. .................... 521/171; 521/172; 521/129; 525/48; 525/49
[58] Field of Search .............. 521/171, 172, 129; 525/48, 49

[56] References Cited

U.S. PATENT DOCUMENTS

| | | | |
|---|---|---|---|
| 3,340,136 | 9/1967 | Burns et al. | 525/49 |
| 3,454,530 | 7/1969 | Case et al. | 260/75 |
| 3,565,812 | 2/1971 | Anderson et al. | 252/182 |
| 3,585,185 | 6/1971 | Levis, Jr. et al. | 260/210 |
| 3,639,541 | 1/1972 | Austin et al. | 260/952 |
| 3,639,542 | 2/1972 | Pizzini et al. | 260/952 |
| 3,642,646 | 2/1972 | Marcus | 252/182 |
| 3,676,376 | 7/1972 | Svoboda et al. | 260/2.5 |
| 3,989,653 | 11/1976 | Baldino et al. | 260/2.5 |
| 4,014,828 | 3/1977 | Thorpe | 525/49 |
| 4,264,745 | 4/1981 | Foucht | 521/171 |

FOREIGN PATENT DOCUMENTS 993451 7/1976 Canada .............. 260/472.3

Primary Examiner—John Kight, III
Assistant Examiner—M. L. Moore
Attorney, Agent, or Firm—Donald L. Johnson; John F. Sieberth; Teresa M. Stanek

[57] ABSTRACT

A normally liquid flame retardant polyol ester prepared by a process comprising reacting a halogen containing anhydride of a dicarboxylic acid or a mixture of said anhydrides with about 2-10 moles of an aliphatic diol or mixture of diols per mole of said anhydride to obtain a substantially fully esterified halogen containing product in which the acid number does not exceed 10 with the optional removal of unreacted diol during the course of the reacting or subsequent to the reacting.

10 Claims, No Drawings

ESTER AND HALOGEN CONTAINING POLYOLS

BACKGROUND OF THE INVENTION

1. Field of the Invention

This invention relates to a novel ester and halogen containing polyol. More particularly, this invention relates to the preparation of a flame retardant polyol and its use in polyurethane compositions.

2. Description of the Prior Art

Polyurethanes are usually obtained by the reaction of di- or polyisocyanates with polyhydroxy compounds, such as polyethers, polyesters or glycols. The problem of the flammability of these polymer compositions has received considerable attention. A variety of compounds are known that provide satisfactory flame resistance, smoke suppression and self-extinguishing properties when added to polyurethane compositions.

It is known that the polyhydroxy compounds themselves which react with the di- or polyisocyanates can be modified to impart flame retardant properties to the resultant polyurethane composition.

Some prior art methods of forming flame retardant polyhydroxy compounds, also known as polyols, involve a two step process. A halogen containing anhydride is combined with a polyol to form a half-ester. The half-ester is then reacted with an alkylene oxide to obtain a polyol.

U.S. Pat. No. 3,642,646 discloses polyol compositions useful in preparing rigid foam compositions. These polyols comprise the reaction adducts of polyfunctional aromatic carboxylic acid anhydrides or chlorendic anhydride and polyether polyols. It specifically teaches the use of half esters based on a polyol and tetrabromophthalic anhydride.

U.S. Pat. No. 3,585,185 discloses a process for preparing ester-containing polyols by the reaction of alkylene oxide condensates of organic compounds having at least two active hydrogen atoms with a halogen-containing organic acid anhydride and an alkylene oxide.

U.S. Pat. No. 3,454,530 teaches the use of polyols useful in the preparation of rigid polyurethane foams. These polyols are prepared by the reaction of a di- or tri-alkanolamine with a cyclic anhydride of an organic dicarboxylic acid and a lower alkylene oxide.

Canadian Pat. No. 993,451 discloses halogen-substituted aromatic amide-ester polyols and their use in a flame retardant flexible polyurethane foam.

U.S. Pat. No. 3,676,376 teaches the use of polyester polyols based on tetrabromophthalic anhydride, an aliphatic dicarboxylic acid, a polyol and an aliphatic diol.

U.S. Pat. Nos. 3,565,812, 3,639,541 and 3,639,542 are directed to the preparation of halogen-containing organic acid anhydrides based on ester- and phosphorous-containing polyols.

U.S. Pat. No. 4,264,745 teaches the use of the reaction product of tetrabromophthalic anhydride, dibromoneopentyl glycol and an alkyloxide.

U.S. Pat. No. 3,989,653 teaches the preparation of simple diesters of tetrabromophthalic anhydride comprising the reaction product of tetrabromophthalic anhydride and a polyhydroxy compound containing at least three hydroxyl groups. Example 3 involves the esterification of tetrabromophthalic anhydride and an aromatic diol.

Copending application S-4991 filed herewith claims a normally liquid flame retardant polyol ester prepared by a process comprising reacting a halogen containing anhydride of a dicarboxylic acid or a mixture of said anhydrides with an aliphatic polyol having at least three hydroxy groups and an aliphatic diol to obtain a substantially fully esterified halogen containing product in which the acid number does not exceed 10 with the optional removal of unreacted diol during the course of the reacting or subsequent to the reacting.

The novel flame retardant polyol prepared by the process of the present invention has an advantage over the flame retardant polyols found in the prior art. Polyols based on halogen containing anhydrides or acids, especially those based on tetrabromophthalic anhydride, have a high viscosity and are difficult to handle by conventional processing methods. Pumps are generally used in the preparation of polyurethane foams. The viscosity of the polyol should preferably be 25,000 cps at 25° C., or lower, to be pumped in a convenient manner. The polyol taught by the present invention is liquid and has a low viscosity and is easily handled by conventional processing techniques.

The halogen and ester containing polyols formed by the practice of the present invention are especially useful in the preparation of flame retardant polyurethane compositions.

SUMMARY OF THE INVENTION

In accordance with the present invention, a normally liquid low viscosity flame retardant polyol can be prepared by the esterification of a halogen containing anhydride of a dicarboxylic acid or a mixture of said anhydrides and 2 to about 10 moles of an aliphatic diol or mixture of diols per mole of said anhydride to obtain a substantially fully esterified halogen containing product in which the acid number does not exceed 10 with the optional removal of unreacted diol during the course of the reacting or subsequent to the reacting.

The flame retardant polyol has at least two free hydroxy groups which react with the —NCO functions of polyisocyanates to form urethane groups. The polyol may also be used to prepare polyesters. The polyurethane or polyester is made flame retardant without the necessity of using additional reactive or additive flame retardant compounds although additional additives can be used.

DESCRIPTION OF THE PREFERRED EMBODIMENTS

The present invention relates to a flame retardant ester and halogen containing polyol for use in polyurethane compositions. A preferred embodiment is a normally liquid flame retardant polyol prepared by a process comprising the esterification of a halogen containing anhydride of a dicarboxylic acid or a mixture of said anhydrides and 2 to about 10 moles of an aliphatic diol or mixture of diols per mole of said anhydride to obtain a substantially fully esterified halogen containing product in which the acid number does not exceed 10 with the optional removal of unreacted diol during the course of the reacting or subsequent to the reacting.

Halogen containing anhydrides of dicarboxylic acids used in preparing the reactive flame retardant polyol of the present invention have the structure:

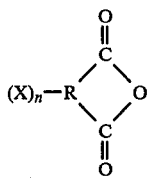

wherein R is a hydrocarbon group having the valence n+2 and is selected from the group consisting of benzene groups, naphthalene groups and alicyclic hydrocarbon groups containing 5 to 10 carbon atoms, X is selected from the group consisting of bromine and chlorine and n is an integer from 1 to 6. Typical halogenated dicarboxylic anhydrides include:

3-chlorophthalic anhydride,
4-bromophthalic anhydride,
3,6-dibromophthalic anhydride,
tetrabromophthalic anhydride,
tetrachlorophthalic anhydride,
1,4,5,6,7,7-hexachlorobicyclo(2.2.1)-5-heptene-2,3-dicarboxylic,
5,6,7,8,9,9-hexachloro-1,2,3,4a,5,8,8a-octahydro-5,8-methano-2,3-naphthalene dicarboxylic anhydride,
1,2,3,4,5,6,7,7-octachloro-3,6-methano-1,2,3,6-tetrahydrophthalic anhydride,
1,4-dichloro-2,3-naphthalene-dicarboxylic anhydride and
1,4-dibromo-2,3-naphthalene-dicarboxylic anhydride.

Mixtures of any of the above anhydrides may also be employed as well as mixtures of the above anhydrides and non-halogenated anhydrides. Preferably, the halogen containing anhydride is tetrahalophthalic anhydride. More preferably, the halogen containing anhydride is tetrabromophthalic anhydride.

It has also been found to be advantageous to include in the reaction mixture a basic material in an amount sufficient to neutralize any residual inorganic acid present in the halogen containing anhydride. An aqueous solution of any material which has a pH greater than about 8 may be employed. Representative materials include, for example, alkali metal and alkaline earth metal hydroxides; carbonates and bicarbonates, such as sodium hydroxide, sodium carbonate, sodium bicarbonate, potassium hydroxide, and calcium carbonate; ammonium hydroxide; and salts such as sodium acetate. Of these, preferred results have been achieved when sodium acetate is employed in the reaction mixture.

Aliphatic diols include alkylene glycols and linear and branched polyether glycols having a plurality of ether linkages containing two hydroxyl groups and being substantially free from functional groups other than hydroxyl groups. Among the diols which are useful in the practice of this invention are ethylene glycol, propylene glycol, butylene glycol, 1,6-hexane diol, and the like.

Preferred diols are the polyether glycols. These are a well-known class of diols and have the formula HOH wherein p is an integer from two to about 100 and R is a divalent aliphatic hydrocarbon group containing about 2 to about 4 carbon atoms. More preferably, R is 2 or 3 carbon atoms. In a highly preferred embodiment R is —CH$_2$CH$_2$— and p is an integer from 2 to 10.

Polyether glycols include polyoxypropylene, polyoxypropylene-oxyethylene and polyoxybutylene diols.

The preferred diols include diethylene glycol, dipropylene glycol, triethylene glycol and tripropylene glycol. Any combination or mixture of diols may be used in the practice of the present invention. The most preferred aliphatic diol is triethylene glycol.

The amount of aliphatic diol used in the practice of the present invention is about 2–10 moles of aliphatic diol or mixture of aliphatic diols per mole of halogen containing anhydride. Preferably, about 3 to 5 and most preferably about 4 moles of aliphatic diol are used.

Although not required, excess diol can optionally be removed during the course of the reaction or subsequent to the completion of the reaction. Excess diol is advantageous because it assists in pushing the esterification to completion.

The reaction should be carried out at a temperature high enough to allow the reaction to proceed, yet not so high as to cause degradation of the reactants or products, a useful range in which to experiment is about 100° C.–250° C. The preferred temperature range is from about 120° C. to about 190° C. At temperatures below about 120° C. very long reaction times are required, whereas, at temperatures above about 190° C. degradation or polymerization of the reactants may occur. A more preferred temperature range is from about 175° C. to about 190° C.

The reaction is considered complete when the acid number approaches zero. However, it is unnecessary to take the reaction to this point and an acid number of 0 to 10 mg KOH/g is generally adequate. Low acid numbers are preferred since this minimizes undesirable side reactions and maximizes the number of hydroxy groups able to bind with the —NCO functions of the polyisocyanate. Completion of the reaction of the present invention is determined by periodically removing samples from the reaction mixture and titrating with base.

In addition to using excess diol to assist in pushing the reaction to completion, products formed as a result of the reaction can be removed to increase reaction rate. Water is formed along with the halogen containing diester polyol of the present invention. By removing water an increase in reaction rate can be achieved. There are at least two ways to remove the water from the reaction system. One way is to evaporate the water by sweeping it out of the reaction system using an inert gas such as nitrogen. Some diol is also removed from the reaction system by this technique. Another method is to azeotropically remove the water using an inert water immiscible solvent. The solvent selected also must possess the proper boiling point to bring the system to the correct temperature. Typical solvents include naptha, xylene, toluene, cumene, heptane decane, and the like.

The reactants may be added concurrently or sequentially. The order of mixing the reactants does not affect the final product obtained.

The ester and halogen containing polyol prepared by the process of the present invention is very useful in making flame retardant, self extinguishing polyurethane compositions. Such compositions are made by reacting a polyisocyanate (eg. toluene diisocyanate, methylenebis-phenylisocyanate, etc.) or polyisocyanate prepolymer with a polyol (eg. polypropylene glycol, hydroxy-terminated polyester, etc.) and optionally a polyamine (eg. methylenebis-ortho chloroaniline, diethylated toluene diamine, etc.). Other ingredients include a catalyst and optionally a blowing agent. In a preferred embodiment the halogen containing polyol of the present invention is substituted for part of or all of the polyol normally used depending upon the degree of flame retardancy needed.

The organic di- or polyisocyanates used in the manufacture of polyurethane are known to the art. Any organic di- or polyisocyanate is suitably employed in producing the flame-retardant compositions of this invention. Combinations of polyisocyanates may also be used. Typical examples of suitable polyisocyanates for use in preparing the flame-retardant polyurethanes of this invention are 1,6-hexamethylene diisocyanate,
1,4-tetramethylene diisocyanate,
m-phenylene diisocyanate,
1-methoxyphenyl-2,3-diisocyanate,
4,4',4''-triphenylmethane triisocyanate,
4,4'-dimethyldiphenylmethane-2,2',5,5'-tetraisocyanate,
toluene diisocyanate and
methylene-bis(phenylisocyanate).

The polyisocyanate may be in the form of a prepolymer. These are generally low molecular weight isocyanate terminated polymer of a diisocyanate and a polyol.

The amount of isocyanate used varies slightly depending upon the nature of the polyurethane being prepared. A sufficient amount of organic polyisocyanate is used to stoichiometrically combine with the polyol to produce polyurethane. In general, the polyisocyanates are employed in amounts that provide from 80 to 150 percent, preferably from 90 to 120 percent of the stoichiometric amount of the isocyanate groups required to react with the reactive hydrogen atoms present on the hydroxyl groups or amino groups of the reactants in the polyurethane-producing reaction mixture.

Any of the conventional catalysts employed in polyurethane technology can be used. Some examples of useful catalysts which can be employed are tertiary amines, such as tetramethyl-1,3-butane diamine, triethylene diamine, triethanolamine, N-methylmorpholine, N-ethylmorpholine, tribenzylamine, N,N-dimethylbenzylamine, as well as tin compounds, such as dibutyl tin dilaurate, stannous oleate, stannous actoate, and others.

In addition to the flame retardant polyol prepared by the process of the present invention, any suitable organic polyol or combination of polyols, including both aliphatic and aromatic may be used, such as polyether polyols and mixtures of polyether polyols and poly(ethylene glycol) adducts of pentaerythritol, sucrose, sorbitol, alphamethylglucoside, butanediol, trimethylolpropane, and the like.

Polyurethanes are used in both the unfoamed and the so-called foam form. The most preferred embodiment of the present invention is a flame retardant, self-extinguishing polyurethane foam comprising the flame retardant polyol of the present invention, sufficient di- or polyisocyanate to combine with said polyol to produce polyurethane foam, a foam-forming catalyst, a blowing agent and optionally additional non-flame retardant polyol.

Polyurethane foams may be either flexible or rigid. Polyurethane foams are normally prepared from diisocyanates and hydroxyl-terminated polyethers or polyesters. Linear or only slightly branched polymers are used to provide flexible foams, whereas more highly branched polymers produce rigid foams. Appropriate catalysts and stabilizers control the foam formation and cure. In general, a foamed polyurethane is produced when low boiling liquids or gaseous blowing agents, are incorporated into, or generated by, the polyurethane-foaming reactants. Blowing agents which may be employed in the preparation of foamed polyurethanes include, for example, water either alone or admixed with other compounds, such as an aqueous solution of the catalyst. When water is employed, it reacts with an excess of the isocyanate to generate carbon dioxide, thereby resulting in a foam. Water is well known as a blowing agent in the preparation of flexible polyurethane foam. Other useful blowing agents especially desirable in rigid polyurethane foams include the chlorinated and fluorinated alkanes having from one to about three carbon atoms, such as the chlorofluoromethanes, the chlorofluoroethanes and the chlorofluorobutanes. The amount of blowing agents employed can be varied over a wide range as is well known to those skilled in the art depending primarily upon the density desired in the foam product.

A wetting agent or surface-active agent is generally necessary for production of high grade polyurethane foam since the foams may collapse or contain very large uneven cells. Numerous wetting agents have been found satisfactory. Non-ionic surfactants are preferred. Examples of common surface active agents include silicone compounds, silicone oil mixtures and the polyethylene glycol ethers of long chain alcohols. For most applications, the surfactant is employed in an amount equal to from about 1.5 to about 2.5 parts by weight per 100 parts by weight of the polyol blend in the foam-forming compositions. An emulsifier may also be used depending on the exact properties of the polyurethane desired.

In preparing a polyurethane composition, one employs a temperature which affords a reasonable rate of reaction and does not cause an untoward amount of undesirable side reactions. The exact reaction temperature employed is not critical. In general, one uses temperatures from about 20° C. to about 350° C. In general, the reaction is conducted under ambient pressures since these are most economical. However, the reaction pressure is not critical. Superatmospheric and subatmospheric pressures can be utilized if desired. In general, vacuum or partial vacuum offers no material advantage. Elevated pressures up to 1,000 psig or more can be utilized when it is desired to conduct the process at a temperature above the normal boiling point of one or more materials in the reaction mixture.

The reaction time is not critical, but depends to some extent on the inherent reactivity of the reactants and other reaction conditions employed. In general, reaction times of from about 15 minutes to ten days are sufficient.

Solvents are not necessary in the preparation of polyurethanes. However, suitable solvents include aromatic hydrocarbons such as benzene, xylene, toluene; the various chlorinated benzenes such as chlorobenzene; dimethoxylene glycol; dimethylformamide; or any other normally liquid material which is also liquid within the above-mentioned temperature range and non-reactive under the reaction conditions.

The flame-retarded urethane polymers of this invention can take the form of foamed products, elastomers, surface coatings and the like. They may be formed in accordance with any of the processing techniques known to the polyurethane art such as the prepolymer, quasi-prepolymer and "one-shot" techniques.

Polyurethane compositions made using the polyols of the present invention are flame retardant and self-extinguishing. However, additional flame retardants compounds may be added to the polyurethane depending on the properties and compositions of the polyurethane desired. These additional flame retardant compounds may include other halogenated organic flame retardants or flame retardant phosphorous compounds well-known in the art.

Flame retardant synergists may also be employed in the preparation of the polyurethane compositions of the present invention. Inorganic synergists include antimony oxide, zinc oxide, zinc borate, and the like. Examples of organic synergists are tris-2-chloro-ethylphosphate, tris-2,3-dibromopropylphosphate, polyammonium phosphate, and the like.

The polymer composition can also have the usual fillers, dyes, pigments, plasticizers, anti-static agents, stabilizing agents, and the like incorporated therein, if desired.

The flame retardant polyol esters of the present invention may also be used to prepare polyesters. The polyols of the present invention are especially useful in unsaturated polyesters.

Typical polyesters of this invention can be made according to the techniques described in the "Encyclopedia of Polymer Science and Technology", Interscience Publishers, New York, N.Y. (1969), Volume II, pages 1–168. Polyester compositions are made from the flame retardant polyol ester of the present invention and aromatic dibasic acids and/or anhydrides. Other dihydric alcohols may be used in addition to the flame retardant polyols of the present invention.

The polyesters are based on prepolymers which may be made by the esterification of dihydric alcohols with unsaturated and modifying dibasic acids and/or anhydrides. The unsaturated polymer is mixed with an unsaturated monomer, e.g., styrene, with which it crosslinks. A catalyst, polymerization inhibitor and inert filler are among the typical additives.

The following examples illustrate the preparation of the flame retardant polyols of the invention.

EXAMPLE 1

Into a 500 ml reaction flask was charged 2.0 g of sodium acetate and 382.9 g (2.55 moles) of triethylene glycol. The system was swept with a stream of nitrogen, the temperature was raised to 130° C. and 394.1 g (0.85 mole) of tetrabromophthalic anhydride was added over a 15 minute period. The temperature was then raised to 180° C. The course of the reaction was followed by periodic acid number determinations. When the acid number decreased to 1.0 the reaction was terminated. The reaction residue weighed 690.8 g. The product was found to have a hydroxyl number of 255.0, a bromine content of 37.73%, and a Brookfield viscosity of 682 cps at 25° C.

EXAMPLE 2

Into a 2 liter reaction flask provided with a Dean and Stark trap was charged 3.4 g sodium acetate and 901.0 g (6.0 moles) triethylene glycol. Into the Dean and Stark trap was added 15.0 g of naptha. The mixture was heated to 130° C. and 695.4 g (1.5 moles) of tetrabromophthalic anhydride was added over a 15 minute period. The reaction mixture was heated to 190° C. and 24.5 g of naphtha was added to maintain reflux. The lower water layer in the Dean and Stark trap was periodically drained until 27.5 ml was collected. At this point the acid number of the reaction mixture was 2.8. The Dean and Stark trap was replaced by a still head, the pressure was reduced to 2.8–4.8 cm of mercury. The reaction mixture was distilled to a residue of 1,101.2 g. The product was found to have an acid number of 0.0, a hydroxyl number of 195.6, a bromine content of 41.43%, and a Brookfield viscosity of 746 cps at 25° C.

Two other batches following the above procedure were run, and the products of all three batches were blended to give a product with a hydroxyl number of 195.9 and a bromine content of 41.11%.

EXAMPLE 3

Into a one liter reaction flask provided with a Dean and Stark trap was charged 2.3 g sodium acetate and 424.5 g (4.0 moles) diethylene glycol. Into the Dean and Stark trap was added 15 g of naptha. The reaction mixture was heated to 130° C. and 463.6 g (1.0 mole) of tetrabromophthalic anhydride was added over a 10 minute period. The contents were then heated to 190° C. and 17.2 g of naptha was added to maintain reflux. The lower water layer in the Dean and Stark trap was periodically drained until 291.0 ml was collected. At this point the acid number of the reaction mixture was 6.8. The Dean and Stark trap was replaced by a still head, and the pressure reduced to 7.9–8.4 cm of mercury. The content was distilled to a residue of 660.7 g. The product was found to have an acid number of 5.9, a hydroxyl number of 172.8, a bromine content of 45.99% and a Brookfield viscosity of 1,460 cps at 25° C.

EXAMPLE 4

Into a 500 ml reaction flask provided with a Dean and Stark trap was charged 1.7 g sodium acetate, 402.5 g (3.0 moles) dipropylene glycol and 20 g xylene. The mixture was heated to 130° C. and 347.7 g (0.75 mole) of tetrabromophthalic anhydride was added over a ten minute period. The mixture was then heated to 190° C. and 65 g of xylene added to maintain reflux. The lower water layer in the Dean and Stark trap was periodically drained until 35.1 ml was collected. At this point the acid number of the reaction mixture was 6.2. The Dean and Stark trap was replaced by a still head, and the pressure reduced to 2.4 cm of mercury. The contents were distilled to a residue of 491.2 g. The product was found to have a hydroxyl number of 190.7, a bromine content of 45.7% and a Brookfield viscosity of 6,700 cps at 25° C.

EXAMPLE 5

Into a one liter reaction flask provided with a Dean and Stark trap was charged 1.4 g sodium acetate, 461.3 g (2.4 moles) tripropylene glycol and 15 g naptha. The reaction mixture was heated to 130° C. and 278.2 g (0.6 mole) of tetrabromophthalic anhydride was added over a 15 minute period. It was then heated to 190° C. and 39.7 g of naptha was added to maintain reflux. When 12.3 ml of lower water layer was in the Dean and Stark trap the acid number was 1.5. At this point the Dean and Stark trap was replaced by a still head and the pressure reduced for distillation. The contents were distilled to a residue of 499.3 g. The product was found to have and acid number of 1.4, a hydroxyl number of 196.2, a bromine content of 37.99%, and a Brookfield viscosity of 906 cps at 25° C.

EXAMPLE 6

Into a 500 ml reaction flask provided with a Dean and Stark trap was charged 2.3 g of sodium acetate, 472.7 g (4 moles) of 1,6-hexanediol and 15.0 g naptha. The mixture was heated to 130° C. and 463.6 g (1.0 mole) of tetrabromophthalic anhydride was added over 30 minutes. It was then heated to 190° C. and 32.7 g of naptha was added to maintain reflux. When 18.0 ml of lower aqueous layer was collected in the Dean and Stark trap the acid number of the reaction mixture was 0.4. At this point the Dean and Stark trap was replaced by a still head and the system was evacuated for distillation. The contents were distilled to a residue of 683.9 g. The product was found to have a hydroxyl number of 199.8, a bromine content of 45.42%, and a Brookfield viscosity of 2,184 at 25° C.

PERFORMANCE DATA

EXAMPLES 7-11

Table 1 contains data on a set of hand mixed polyurethane foam compositions containing the flame retardant polyol from Example 1. Other ingredients used in preparing the foam include:

Poly G 71-530, a trademark of Olin Chemicals, which is a sucrose-amine type polyether polyol with a hydroxyl number of 530±10.

Dow Corning 193, a registered trademark of Dow Corning Corporation, which is a nonhydrolyzable silicone glycol copolymer surfactant designed for use in producing all types of rigid urethane foam.

Polycat 8, a trademark of Abbott Laboratories, refers to N,N'-dimethylcyclohexylamine, a tertiary amine catalyst.

T-12, a trademark of M and T Chemicals, refers to a dibutyl tin dilaurate catalyst containing 18% $Sn^{IV}$.

Freon 11B, available from E. I. duPont deNemours and Co., Inc., refers to trichlorofluoromethane, a blowing agent.

PAPI 135, a trademark of Upjohn Polymer Chemicals, refers to a polymethylene polyphenylisocyanate with an average functionality of 2.7.

The flame retardant polyol as prepared in Example 1, Poly G 71-530, Dow Corning 193, Polycat 8, T-12 and Freon 11B were weighed and charged into a plastic container. The mixture was blended for 45 seconds with an electric mixer. PAPI 135 was then weighed and added to the mixture and blended for 15 seconds. The mixture was then transferred to a cardboard box and the foam was allowed to rise. The entire procedure was carried out at room temperature.

Two tests were used to evaluate the flame retardant properties of these polyurethane foam compositions. They were the ASTM D-1692 and the Oxygen Index Test. ASTM D-1692 is a small scale horizontal laboratory screening procedure for measuring the rate of burning or extent of burning of rigid or flexible cellular plastics such as polyurethane foams. The Oxygen Index Test is defined as the minimal volume fraction of oxygen in a slowly rising gaseous atmosphere that will sustain the candlelike burning of a stick of polymer. The higher the Oxygen Index of a molded article, the more flame retardant it is.

The composition of each foam is given in parts by weight.

TABLE I

| Example | 7 | 8 | 9 | 10 | 11 |
|---|---|---|---|---|---|
| Polyol from Example 1 | — | 25.0 | 33.0 | 50.0 | 100.0 |
| 71-530 | 100.0 | 75.0 | 67.0 | 50.0 | — |
| DC-193 | 1.5 | 3.0 | 3.0 | 3.0 | 3.0 |
| Polycat 8 | 2.5 | 0.7 | 0.7 | 0.7 | 0.4 |
| T-12 | — | 0.05 | 0.05 | 0.05 | 0.05 |
| Freon 11B | 40.0 | 32.0 | 32.0 | 32.0 | 32.0 |
| PAPI 135 | 138.8 | 128.0 | 121.5 | 107.5 | 66.6 |
| Isocyanate Index, % | 110.0 | 117.0 | 116.0 | 115.0 | 110.0 |
| Density, lbs./cu. ft. | 1.9 | 2.1 | 2.0 | 1.9 | 2.3 |
| Oxygen Index | 20.2 | 21.8 | 21.8 | 21.8 | 24.5 |
| D-1692 burn rate in./minute | 7.5 | 1.7 | 2.4 | 1.8 | 1.2 |
| D-1692 extent of burn, in. | 5.0 | 1.1 | 1.6 | 1.2 | 0.5 |

As indicated in Table I, the polyurethane foam samples which contain a larger amount of flame retardant polyol from Example 1 demonstrate improved flame retardant properties when evaluated by the Oxygen Index and ASTM D-1692 burn tests.

EXAMPLES 12-17

Table II contains data on a set of hand mixed polyurethane foam compositions containing the flame retardant polyol from Example 2. These foams were prepared in the same manner and with the same ingredients described in Examples 7-11.

TABLE II

| Example | 12 | 13 | 14 | 15 | 16 | 17 |
|---|---|---|---|---|---|---|
| Polyol from Example 2 | 0.0 | 20.0 | 40.0 | 60.0 | 80.0 | 100.0 |
| 71-530 | 100.0 | 80.0 | 60.0 | 40.0 | 20.0 | — |
| DC-193 | 3.0 | 3.0 | 3.0 | 3.0 | 3.0 | 3.0 |
| Polycat 8 | 2.5 | 2.0 | 1.5 | 1.0 | 1.0 | 0.5 |
| T-12 | 0.03 | 0.03 | 0.03 | 0.03 | 0.03 | 0.03 |
| Freon 11B | 38.0 | 35.0 | 32.5 | 29.7 | 27.0 | 26.0 |
| PAPI 135 | 139.0 | 121.0 | 104.0 | 86.0 | 69.0 | 51.0 |
| Isocyanate Index, % | 110.0 | 110.0 | 110.0 | 110.0 | 110.0 | 110.0 |
| Density, lbs./cu. ft. | 1.8 | 1.8 | 1.9 | 2.0 | 2.3 | — |
| Oxygen Index | 20.0 | 20.8 | 21.8 | 22.7 | 23.5 | 25.9 |
| D-1692 burn rate in./minute | 4.2 | 3.4 | 1.9 | 1.3 | 1.2 | 1.4 |
| D-1692 extent of burn, inches | 6.0 | 5.5 | 1.5 | 0.8 | 0.8 | 1.1 |

As indicated in Table II, the polyurethane foam samples which contain a larger amount of flame retardant polyol from Example 2 demonstrate improved flame retardant properties when evaluated by the Oxygen Index and ASTM D-1962 burn tests.

EXAMPLES 18-22

Table III contains data on a set of hand mixed polyurethane foam compositions containing the flame retardant polyol from Example 3. These foams were prepared in the same manner and with the same ingredients as described in Examples 7-11.

TABLE III

| Example | 18 | 19 | 20 | 21 | 22 |
|---|---|---|---|---|---|
| Polyol from Example 3 | 0.0 | 20.0 | 40.0 | 60.0 | 20.0 |
| 71-530 | 100.0 | 80.0 | 60.0 | 40.0 | 80.0 |
| DC-193 | 3.0 | 3.0 | 3.0 | 3.0 | 3.0 |
| Polycat 8 | 2.0 | 1.8 | 1.7 | 1.5 | 1.7 |
| T-12 | 0.03 | 0.03 | 0.04 | 0.03 | 0.04 |
| Freon 11B | 34.0 | 32.0 | 29.0 | 26.0 | 24.0 |
| PAPI 135 | 139.0 | 120.0 | 101.0 | 83.0 | 64.0 |
| Isocyanate Index, % | 110.0 | 110.0 | 110.0 | 110.0 | 110.0 |
| Density, lbs./cu. ft. | 2.4 | 1.9 | 1.9 | 2.0 | 2.5 |
| D-1692 burn rate in./minute | 4.5 | 2.2 | 1.1 | 1.1 | 0.5 |
| D-1692 extent of | 6.0 | 2.6 | 0.7 | 0.5 | 0.25 |

TABLE III-continued

| Example | 18 | 19 | 20 | 21 | 22 |
|---|---|---|---|---|---|
| burn, inches | | | | | |

As indicated in Table III, the polyurethane foam samples which contain a larger amount of flame retardant polyol from Example 3 demonstrate improved flame retardant properties when evaluated by the ASTM D-1692 burn test.

EXAMPLES 23-26

Table IV contains data on a set of hand mixed polyurethane foam compositions containing the flame retardant polyol from Example 4. These foams were prepared in the same manner and with the same ingredients as described in Examples 7-11.

TABLE IV

| Example | 23 | 24 | 25 | 26 |
|---|---|---|---|---|
| Polyol from Example 4 | 0.0 | 20.0 | 40.0 | 60.0 |
| 71-530 | 100.0 | 80.0 | 60.0 | 40.0 |
| DC-193 | 3.0 | 3.0 | 3.0 | 3.0 |
| Polycat 8 | 2.0 | 2.0 | 2.0 | 2.0 |
| T-12 | 0.03 | 0.03 | 0.03 | 0.03 |
| Freon 11B | 34.0 | 32.0 | 29.0 | 27.0 |
| PAPI 135 | 139.0 | 121.0 | 103.0 | 85.0 |
| Isocyanate Index, % | 110.0 | 110.0 | 110.0 | 110.0 |
| Density, lbs./cu. ft. | 2.4 | 3.0 | 3.8 | 2.5 |
| D-1692 burn rate in./minute | 4.5 | 1.0 | 0.9 | 1.2 |
| D-1692 extent of burn, inches | 6.0 | 1.0 | 0.7 | 0.5 |

As indicated in Table IV, the polyurethane foam samples which contain a larger amount of flame retardant polyol from Example 4 demonstrate improved flame retardant properties when evaluated the ASTM D-1692 burn test.

EXAMPLES 27-28

Table V contains data on a set of hand mixed polyurethane foam compositions containing the flame retardant polyol from Example 5. These foams were prepared in the same manner and with the same ingredients as described in Examples 7-11.

TABLE V

| Example | 27 | 28 |
|---|---|---|
| Polyol from Example 5 | 0.0 | 20.0 |
| 71-530 | 100.0 | 80.0 |
| DC-193 | 3.0 | 3.0 |
| Polycat 8 | 2.0 | 1.8 |
| T-12 | 0.03 | 0.03 |
| Freon 11B | 34.0 | 32.0 |
| PAPI 135 | 139.0 | 121.0 |
| Isocyanate Index, % | 110.0 | 110.0 |
| Density, lbs./cu. ft. | 2.0 | 3.9 |
| D-1692 burn rate in./minutes | 3.6 | 1.7 |
| D-1692 extent of burn, inches | 6.0 | 3.0 |

As indicated in Table V, the polyurethane foam samples which contain a larger amount of flame retardant polyol from Example 5 demonstrate improved flame retardant properties when evaluated by the ASTM D-1692 burn test.

EXAMPLES 29-33

Table VI contains data on a set of hand mixed polyurethane foam compositions containing the flame retardant polyol from Example 6. These foams were prepared in the same manner and with the same ingredients as described in Examples 7-11.

TABLE VI

| Example | 29 | 30 | 31 | 32 | 33 |
|---|---|---|---|---|---|
| Polyol from Example 6 | 0.0 | 20.0 | 40.0 | 60.0 | 80.0 |
| 71-530 | 100.0 | 80.0 | 60.0 | 40.0 | 20.0 |
| DC-193 | 3.0 | 3.0 | 3.0 | 3.0 | 3.0 |
| Polycat 8 | 2.0 | 2.0 | 2.0 | 2.0 | 1.1 |
| T-12 | 0.03 | 0.03 | 0.04 | 0.03 | 0.03 |
| Freon 11B | 34.0 | 32.0 | 29.0 | 27.0 | 25.0 |
| PAPI 135 | 139.0 | 121.0 | 104.0 | 87.0 | 70.0 |
| Isocyanate Index, % | 110.0 | 110.0 | 110.0 | 110.0 | 110.0 |
| Density, lbs./cu. ft. | 2.0 | 1.8 | 1.9 | 1.9 | 2.6 |
| D-1692 burn rate in./minutes | 3.6 | 2.5 | 1.3 | 1.2 | 1.1 |
| D-1692 extent of burn, inches | 6.0 | 3.0 | 0.8 | 0.5 | 0.5 |

As indicated in Table VI, the polyurethane foam samples which contain a larger amount of flame retardant polyol from Example 6 demonstrate improved flame retardant properties when evaluated by the ASTM D-1692 burn test.

I claim:

1. A normally liquid flame retardant polyol ester prepared by a process consisting essentially of reacting a halogen containing anhydride of a dicarboxylic acid or a mixture of said anhydrides wherein said anhydride has the structure:

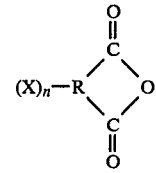

wherein R is a hydrocarbon group having the valence n+2 and is selected from the group consisting of benzene groups, naphthalene groups and alicyclic hydrocarbon groups containing 5 to 10 carbon atoms, X is selected from the group consisting of bromine and chlorine and n is an integer from 1 to 6, with 2 to about 10 moles of an aliphatic diol or mixture of diols per mole of said anhydride at a temperatue of about 100° C. to 250° C. to obtain a substantially fully esterified halogen containing product in which the acid number does not exceed 10 with the optional removal of unreacted diol during the course of the reacting or subsequent to the reacting.

2. A polyol ester, as recited in claim 1, wherein said anhydride is tetrahalophthalic anhydride.

3. A polyol ester, as recited in claim 2, wherein said tetrahalophthalic anhydride is tetrabromophthalic anhydride.

4. A polyol ester, as recited in claim 3, wherein said diol is a polyalkylene glycol having the formula

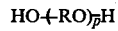

wherein p is an integer from two to about 100 and R is a divalent aliphatic hydrocarbon group containing about 2 to about 4 carbon atoms.

5. A polyol ester, as recited in claim 4, wherein said diol is triethylene glycol.

6. A polyol ester, as recited in claim 5, wherein 4 moles of triethylene glycol are added per mole of tetrabromophthalic anhydride.

7. A polyol ester, as recited in claim 6, wherein about 2 moles of triethylene glycol per mole of tetrabromophthalic anhydride are removed during or subsequent to the reacting.

8. A polyurethane composition comprising the reaction product of said flame retardant polyol ester of claim 1 and a diisocyanate, polyisocyanate or isocyanate terminated pre-polymer.

9. A flame retardant, self-extinguishing polyurethane made by reacting a mixture comprising:
(a) said flame retardant polyol ester of claim 1,
(b) organic diisocyanate, polyisocyanate or isocyanate terminated pre-polymer at least sufficient to react with said polyol to produce polyurethane, and
(c) a catalyst.

10. A flame retardant, self-extinguishing polyurethane foam made by reacting a mixture comprising:
(a) said flame retardant polyol ester of claim 1,
(b) organic diisocyanate, polyisocyanate or isocyanate terminated pre-polymer at least sufficient to react with said polyol to produce polyurethane,
(c) a foam-forming catalyst, and
(d) a blowing agent.

* * * * *